(12) United States Patent
Wingen et al.

(10) Patent No.: US 6,682,785 B2
(45) Date of Patent: Jan. 27, 2004

(54) FLUORINATED ANTHRACENES, AND THEIR USE IN LIQUID-CRYSTAL MIXTURES

(75) Inventors: Rainer Wingen, Hattersheim (DE); Barbara Hornung, Hasselroth (DE); Wolfgang Schmidt, Dreieich (DE)

(73) Assignee: Clariant Finance (BVI) Limited (VG)

( * ) Notice: Subject to any disclaimer, the term of this patent is extended or adjusted under 35 U.S.C. 154(b) by 0 days.

(21) Appl. No.: 10/241,882

(22) Filed: Sep. 12, 2002

(65) Prior Publication Data

US 2003/0118749 A1 Jun. 26, 2003

(30) Foreign Application Priority Data

Sep. 17, 2001 (DE) ......................................... 101 45 778

(51) Int. Cl.[7] ........................ C09K 19/32; C07C 25/18; C07C 22/08; C07C 23/18; C07C 25/22

(52) U.S. Cl. ................... 428/1.1; 252/299.62; 570/183; 570/187; 570/188

(58) Field of Search ....................... 252/299.62, 299.61, 252/299.63; 428/1.1; 570/183, 187, 188; 549/369

(56) References Cited

U.S. PATENT DOCUMENTS

| | | | | |
|---|---|---|---|---|
| 4,798,680 A | 1/1989 | Nohira et al. | ........... | 252/299.01 |
| 5,550,236 A | 8/1996 | Schlosser et al. | ........... | 544/238 |
| 5,744,060 A | 4/1998 | Tarumi et al. | ......... | 252/299.63 |
| 5,800,734 A | 9/1998 | Buchecker et al. | ..... | 252/299.61 |
| 5,997,766 A | 12/1999 | Kirsch et al. | .......... | 252/299.61 |
| 6,083,573 A | 7/2000 | Tarumi et al. | ............... | 428/1.1 |

FOREIGN PATENT DOCUMENTS

| | | |
|---|---|---|
| DE | 44 27 266 | 2/1995 |
| DE | 195 28 085 | 2/1996 |
| DE | 195 31 165 | 3/1996 |
| DE | 195 28 665 | 2/1997 |
| DE | 195 32 292 | 3/1997 |
| DE | 196 07 996 | 9/1997 |
| DE | 196 54 487 | 7/1998 |
| DE | 100 50 071 | 6/2001 |
| EP | 0 318 423 | 5/1989 |
| EP | 0 355 008 | 2/1990 |
| EP | 0 552 658 | 7/1993 |
| EP | 0 665 825 | 8/1995 |
| EP | 0 736 513 | 10/1996 |
| EP | 0 893 424 | 1/1999 |
| EP | 0 915 144 | 5/1999 |
| WO | WO 88/00938 | 2/1988 |
| WO | WO 92/11241 | 7/1992 |
| WO | WO 96/00710 | 1/1996 |
| WO | WO 96/30344 | 10/1996 |
| WO | WO 00/36054 | 6/1999 |

OTHER PUBLICATIONS

Ichinose, H., et al., "High optical anisotrophy and small rotational viscosity LC mixture for field–sequential color TN–LCDs", Seventh International Display Workshop, Nov. 25—Dec. 1, 2000, Kobe, Japan, IDW '00, pp. 77–80.

Meyer, A.Y., et al., "Planar and nonplanar unsaturation, preparation, properties, and molecular–orbital charachterization of some fluoro–derivative of anthracene and anthraquinone", Israel Journal of Chemistry, vol. 11, No. 6, 1973, pp. 791–804.

Hankinson, B., et al., "Aryne chemistry. Part XXX. Approaches to the synthesis of 9–alkyl and 9,10–dialkyl–1,2,3,4,5,6,7,8–octafluoro–9,10–dihydro–9,10–o–benzenoanthracenes (9–alkyl– and 9/10–dialkyl–1,2,3,4,5,6,7,8–octafluorotriptycenes)", J.C.S. Perkin I, 1972, pp. 2372–2377.

Haenel, Matthias W., et al., "Facile syntheses of 1,8–Bis-(diphenylphosphino)anthracene and 1,8–Bis(dimethylamino)anthracene by nucleophilic substitution of 1,8–difluoroanthracene", Synlett, Mar. 1998, pp. 301–303.

Olsen, Robert J., et al., "A photoannulation route to naphthalenes from cyclic ketones", J. Org. Chem., 1991, 56, pp. 989–991.

Sakagami Sakumitsu, et al., "Mesomorphic properties of 2–(4–n–Alkoxybenzylideneamino)anthracenes", Bulletin of the Chemical Society of Japan, vol. 50(4), pp. 1009–1010 (1977).

Sigreist, A.E. von, et al., "Uber die darstellung von styryl–derivaten aus methyl–substituierten carbocyclischen aromaten", Helvetica Chimica Acta, vol. 52, fasc. 8 (1969), No. 253–254, pp. 2521–2554.

Cantrell, Gary L., "Synthesis of 1,2,3,4–tetrafluoro– and 1,2,3,4,5,6,7,8–octafluoroanthracenes via cycloaddition–revision", Journal of Fluorine Chemistry, 29 (1985), pp. 417–424.

Gray, G.W., et al., "The synthesis of several lateral difluoro–substituted 4,4"–dialkyl– and 4,4"–alkoxyalkyl–terphenyls and a rationalisation of the effect of such substitution on mesophase type and transition temperatures", Mol. Cryst. Liq. Cryst., 1991, vol. 204, pp. 43–64.

Bezborodov, V.S., et al., "The synthesis and properties of some mesomorphic cyclohexene derivatives" Liquid Crystals, 1997, vol. 23, No. 1, pp. 69–75.

Hird, Michael, et al., "The relationship between molecular structure and mesomorphic properties of 2,2'—and 3,2 –difluoroterphenyls synthesized by palladium–catalysed cross–couplings", Liquid Crystals 1995, vol. 18, No. 1, pp. 1–11.

(List continued on next page.)

*Primary Examiner*—Shean C. Wu
(74) *Attorney, Agent, or Firm*—Alan P. Kass

(57) ABSTRACT

The invention relates to compounds of the formula (I) having a fluorinated anthracene or fluorinated tetrahydroanthracene core structure and to liquid-crystal mixtures comprising these compounds and to the use thereof in liquid-crystal displays.

16 Claims, No Drawings

OTHER PUBLICATIONS

Cha, Jin Soon, et al., "Preparations of aldehydes from carboxylic esters by reductive oxidations with lithium aluminum hydride and pyridinium chlorochromate or pyridinium dichromate", Bull. Korean Chem. Soc., 1999, vol. 20, No. 11, pp. 1373–1374.

Collins, J.C., "Dipyridine–chromium(VI) oxide oxidation of alcohols in dichloromethane", Trtrahedron Letter, No. 30, 1968, pp. 3363–3366.

Colley, Robert A., "Linear and network polymer electrolytes based on low melting prepolymers", J. Mater. Chem., 1999, 9, pp. 1661–1667.

Mitchell, Riginald H., et al., "Syntheses and reactions of the first dithia [3.1.3.1]metacyclophanes, [2.1.2.1]metacyclophanes, and [2.1.2.1]metacyclophanedienes", J. Org. Chem., 1984, 49, pp. 2534–2540.

Li, Min–Hui, et al., "Blue phases and twist grain boundary phases (TGBA and TGBC) in a series of fluoro-substituted chiral tolane derivatives", Liquid Crystals, 1997, vol. 23, No. 3, pp. 389–408.

Bahadur, Birendra, Liquid Crystals Applications and Uses, World Scientific Publishing, vol. 1, 1990, pp. 410–411.

Prince, C., "AMLCDs", SID Inter. Sympos. 1997, vol. 1, pp. m–3/3–m–3/37.

Walton, Henry M., "Reaction of peroxyacetic acid with α–Aralkylidenecyclanones", J. Organic Chemistry, 22, Oct. 1957, pp. 1161–1165.

Organikum, Organisch–Chemisches Grundpraktikum, Berlin 1994, pp. 612–616.

Braude, E.A., et al., "Hydrogen transfer. Prt IV. The use of quinones of high potential as dehydrogenation reagents", J. Chem. Soc., 1954, pp. 3569–3574.

Lueder, E., "S2–1 Invited Address Recent Progress of AML-CDs", ASIA Display, 1995, pp. 9–12.

Anderson, Benjamin A., et al., "Palladium–catalyzed cross coupling reactions of oxazol–2–ylzinc chloride derivatives", Synthesis, May 1996, pp. 583–585.

FLUORINATED ANTHRACENES, AND THEIR USE IN LIQUID-CRYSTAL MIXTURES

For an increasing number of applications of LCDs—for example for use in automobiles, in which a temperature range of from −40° C. to 100° C. can readily occur, but also for portable equipment, such as mobile telephones and notebook PCs—there is a need for liquid-crystal mixtures which on the one hand have a very broad working-temperature range and on the other hand have the lowest possible threshold voltage.

There is therefore a continuing demand for novel, suitable liquid-crystal mixtures and mixture components. As described in Ichinose et al. (IDW 00, Abstr. LCT4-3) or in DE-A-10 050 071, materials are being sought in which high optical anisotropy (Δn) and low rotational viscosity coexist—with other parameters, such as, for example, high absolute values of the dielectric anisotropy (Δε), likewise being required in addition to further applicationally relevant parameters.

The object of the present invention is therefore to provide novel components for use in nematic or cholesteric or chiral-smectic liquid-crystal mixtures which have high absolute values of the dielectric anisotropy combined with a favorable ratio of viscosity and clearing point. In addition, the compounds should to a large extent be light- and UV-stable and thermally stable. Furthermore, they should be suitable for achieving a high "voltage holding ratio (VHR)". They should furthermore be readily accessible synthetically and therefore potentially inexpensive.

The anthracene derivatives having 2-(4-subst.)styryl substituents (Helv. Chim. Acta 52, 2521 (1969)) or 2-(4-subst.) benzylidenamino substituents (Bull. Chem. Soc. Jpn. 50, 1009 (1977)), the known derivatives of 1,2,3,4-tetrahydroanthracene (J. Org. Chem. 56, 989 (1991)), the known mono- and difluoroanthracenes {Isr. J. Chem. 11, 791 (1973); Synlett 1998, 301}, tetrafluorotetrahydroanthracenes (J. Chem. Soc. Perkin Trans. 1 1972, 2372), tetrafluoroanthracenes (J. Fluorine Chem. 29, 417, 1985), the 9,10-diphenylanthracenes (JP-A 61 281 193), substituted anthracene (EP 915 144) and the cholesterol esters of anthracene (WO 88/00938), do not suggest to the person skilled in the art that fluorine-substituted derivatives of these ring systems are suitable as a component of liquid-crystal mixtures.

The present invention relates to compounds of the formula (I) and to liquid-crystal mixtures comprising these compounds

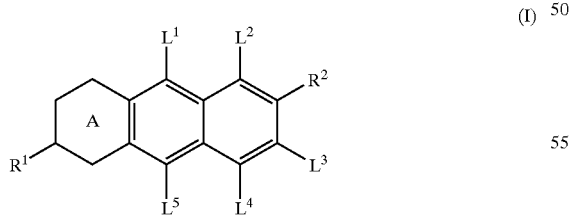

(I)

in which:
$L^1$, $L^2$, $L^3$, $L^4$ and $L^5$ are identical or different and are H or F, with the provisos that
  a) at least one of $L^1$, $L^2$, $L^3$ $L^4$ and $L^5$ must be F
  b) if $L^1$ is F, $L^3$, $L^4$ and $L^5$ must be H
  c) if $L^4$ or $L^5$ is F, $L^1$ and $L^2$ must be H,
$R^1$ is a straight-chain or branched alkyl radical having from 1 to 16 carbon atoms or a straight-chain or branched alkenyl radical having from 2 to 16 carbon atoms, in which
  a) one or more non-adjacent and non-terminal $CH_2$ groups may be replaced by —O—, —C(=O)O—, —O—C(=O)—, —O—C(=O)—O—, —C(=O)— or —Si(CH_3)_2—, and/or
  b) one $CH_2$ group may be replaced by —C≡C—, cyclopropane-1,2-diyl, cyclobutane-1,3-diyl, cyclohexan-1,4-diyl or phenylene-1,4-diyl, and/or
  c) one or more H atoms may be replaced by F and/or Cl,
$R^2$ is hydrogen, F, Cl, CN, —NCS, $CF_3$, $CHF_2$, $CH_2F$, $OCF_3$, $OCHF_2$, $OCH_2F$, $OCH_2CF_3$, OCH=CF_2 or a straight-chain or branched alkyl radical having from 1 to 12 carbon atoms or a straight-chain or branched alkenyl radical having from 2 to 12 carbon atoms, in which
  a) one or more non-adjacent and non-terminal $CH_2$ groups may be replaced by —O—, —C(=O)O—, —O—C(=O)—, —O—C(=O)—O—, —C(=O)— or —Si(CH_3)_2—, and/or
  b) one $CH_2$ group may be replaced by —C≡C—, cyclopropane-1,2-diyl or cyclobutane-1,3-diyl, and/or
  c) one or more H atoms may be replaced by F and/or Cl and/or the -$M^2$-$A^2$-$R^3$ group, in which
    $M^2$ is —CO—O—, —O—CO—, —$CH_2$—O—, —O—$CH_2$—, —$CF_2$—O—, —CH=CH—, —CF=CF—, —C≡C—, —$CH_2$—$CH_2$—CO—O—, —O—CO—$CH_2$—$CH_2$—, —$CH_2$—$CH_2$—, —$CF_2$—$CF_2$—, —$(CH_2)_4$—, —OC(=O)CF=CF— or a single bond,
    $A^2$ is 1,4-phenylene, in which one or two H atoms may be replaced by F, Cl, CN and/or $OCF_3$ or up to three H atoms may be replaced by fluorine, 1,4-cyclohexylene, in which one or two H atoms may be replaced by $CH_3$ and/or F, 1-cyclohexene-1,4-diyl, in which one H atom may be replaced by $CH_3$ or F, or 1,3-dioxane-2,5-diyl,
    $R^3$ has the same possible meanings as $R^2$, with the exception of -$M^2$-$A^2$-$R^3$,

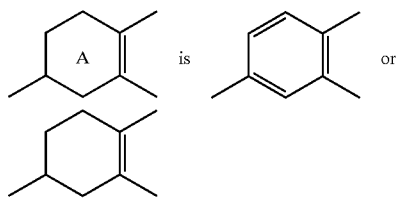

Preference is given to the compounds of the formulae (Ia) to (It):

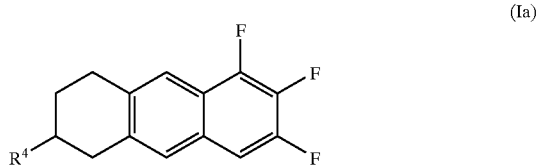

(Ia)

US 6,682,785 B2

3
-continued (Ib)
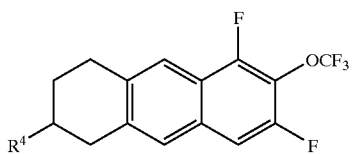

(Ic)
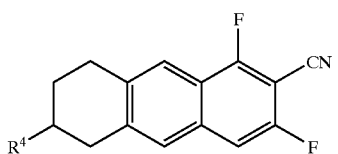

(Id)
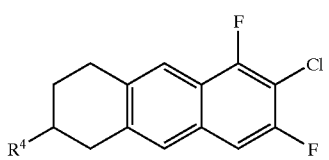

(Ie)
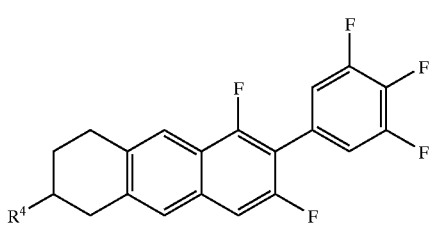

(If)
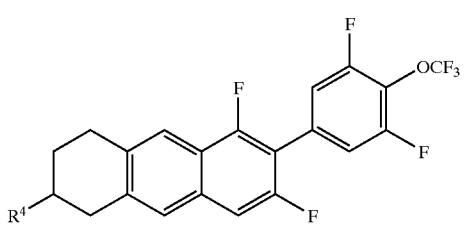

(Ig)
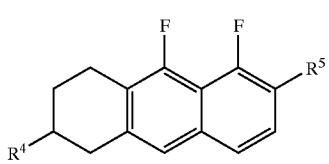

(Ih)
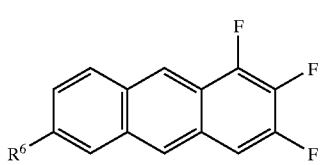

(Ii)
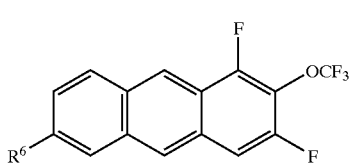

(Ik)
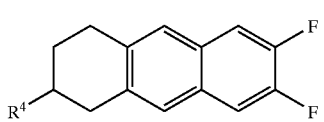

4
-continued (Im)
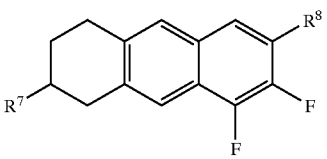

(In)
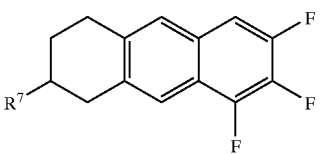

(Io)
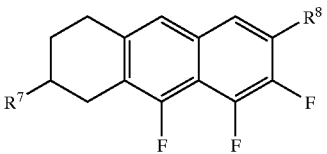

(Ip)
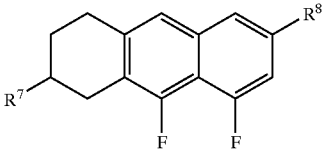

(Iq)
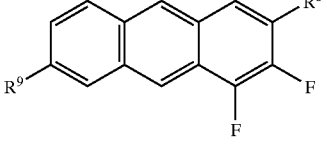

(Ir)
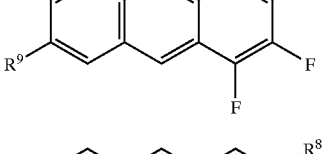

(Is)

(It)
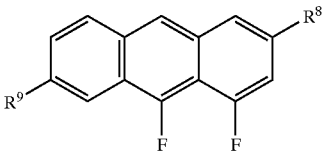

in which
$R^4$ is a straight-chain or branched alkyl radical having from 1 to 16 carbon atoms or a straight-chain or branched alkenyl radical having from 2 to 16 carbon atoms, in which one non-terminal $CH_2$ group may be replaced by —O— and/or one $CH_2$ group may be replaced by cyclohexane-1,4-diyl or phenylene-1,4-diyl, $R^5$ is hydrogen, a straight-chain or branched alkyl radical having from 1 to 12 carbon atoms or a straight-chain or branched alkenyl radical having from 2 to 12 carbon atoms, in which a) one or more non-adjacent and non-terminal $CH_2$ groups may be replaced by —O—, —C(=O)O—, —O—C(=O)— or —Si($CH_3$)$_2$—, and/or b) one $CH_2$ group may be replaced by —C≡C—, cyclopropane-1,2-diyl or cyclobutane-1,3-diyl, and/or c) one or more H atoms may be replaced by F and/or Cl, or the -$M^2$-$A^2$-$R^3$ group, in which $M^2$ is —CO—O—, —O—CO—, —$CH_2$—O—, —O—$CH_2$—, —$CF_2$—O—, —O—$CF_2$—, —$CH_2$—$CH_2$—CO—O—, —O—CO—$CH_2$—$CH_2$—, —$CH_2$—$CH_2$—, —$CF_2$—$CF_2$—, —($CH_2$)$_4$—, —OC(=O)CF=CF—, or a single bond, $A^2$ is 1,4-cyclohexylene, in which one or two H atoms may be replaced by $CH_3$ and/or F, 1-cyclohexene-1,4-diyl, in which one H atom may be replaced by $CH_3$ or F, or 1,3-dioxane-2,5-diyl, $R^3$ is hydrogen, a straight-chain or branched alkyl radical having from 1 to 12 carbon atoms or a straight-chain or branched alkenyl radical having from 2 to 12 carbon atoms, in which a) one or more non-adjacent and non-terminal $CH_2$ groups may be replaced by —O—, —C(=O)O—, —O—C(=O)—, or —Si($CH_3$)$_2$—, and/or b) one $CH_2$ group may be replaced by —C≡C—, cyclopropane-1,2-diyl or cyclobutane-1,3-diyl, and/or c) one or more H atoms may be replaced by F and/or Cl, $R^6$ is a straight-chain or branched alkyl radical having from 1 to 12 carbon atoms, in which a) one or more non-adjacent and non-terminal $CH_2$ groups may be replaced by —O—, —C(=O)O—, —O—C(=O)—, or —Si($CH_3$)$_2$—, and/or b) one $CH_2$ group which is not adjacent to the ring system may be replaced by —C≡C— or —CH=CH—, and/or c) one —$CH_2$— group may be replaced by cyclopropane-1,2-diyl, cyclobutane-1,3-diyl or cyclohexane-1,4-diyl or 1,3-dioxane-2,5-diyl, and/or d) one or more H atoms may be replaced by F and/or Cl, $R^7$ is a straight-chain or branched alkyl radical having from 1 to 16 carbon atoms or a straight-chain or branched alkenyl radical having from 2 to 16 carbon atoms, in which one non-terminal $CH_2$ group may be replaced by —O— and/or one $CH_2$ group may be replaced by cyclohexane-1,4-diyl or phenylene-1,4-diyl, $R^8$ is hydrogen, a straight-chain or branched alkyl radical having from 1 to 12 carbon atoms or a straight-chain or branched alkenyl radical having from 2 to 12 carbon atoms, in which a) one or more non-adjacent and non-terminal $CH_2$ groups may be replaced by —O—, —C(=O)O—, —O—C(=O)— or —Si($CH_3$)$_2$—, and/or b) one $CH_2$ group may be replaced by —C≡C—, cyclopropane-1,2-diyl or cyclobutane-1,3-diyl, and/or c) one or more H atoms may be replaced by F and/or Cl, or the -$M^3$-$A^3$-$R^{10}$ group, in which $M^3$ is —CO—O—, —O—CO—, —$CH_2$—O—, —O—$CH_2$—, —$CF_2$—O—, —O—$CF_2$—, —$CH_2$—$CH_2$—CO—O—, —O—CO—$CH_2$—$CH_2$—, —$CH_2$—$CH_2$—, —$CF_2$—$CF_2$—, —($CH_2$)$_4$—, —OC(=O)CF=CF— or a single bond, $A^3$ is 1,4-cyclohexylene, in which one or two H atoms may be replaced by $CH_3$ and/or F, 1-cyclohexene-1,4-diyl, in which one H atom may be replaced by $CH_3$ or F, or 1,3-dioxane-2,5-diyl, $R^{10}$ is hydrogen, a straight-chain or branched alkyl radical having from 1 to 12 carbon atoms or a straight-chain or branched alkenyl radical having from 2 to 12 carbon atoms, in which a) one or more non-adjacent and non-terminal $CH_2$ groups may be replaced by —O—, —C(=O)O—, —O—C(=O)—, or —Si($CH_3$)$_2$—, and/or b) one $CH_2$ group may be replaced by —C≡C—, cyclopropane-1,2-diyl or cyclobutane-1,3-diyl, and/or c) one or more H atoms may be replaced by F and/or Cl, $R^9$ is a straight-chain or branched alkyl radical having from 1 to 12 carbon atoms, in which a) one or more non-adjacent and non-terminal $CH_2$ groups may be replaced by —O—, —C(=O)O—, —O—C(=O)—, or —Si($CH_3$)$_2$—, and/or b) one $CH_2$ group which is not adjacent to the ring system may be replaced by —C≡C— or —CH=CH—, and/or c) one —$CH_2$— group may be replaced by cyclopropane-1,2-diyl, cyclobutane-1,3-diyl or cyclohexane-1,4-diyl or 1,3-dioxane-2,5-diyl, and/or d) one or more H atoms may be replaced by F and/or Cl.

The provision of compounds of the formula (I) very generally considerably broadens the range of liquid-crystalline substances which are suitable from various applicational points of view for the preparation of liquid-crystalline mixtures.

In this connection, the compounds of the formula (I) have a broad range of applications. Depending on the choice of substituents, they can be added to other classes of compound in order, for example, to modify the dielectric and/or optical anisotropy of a dielectric of this type. They can also serve to optimize its threshold voltage and/or its viscosity.

Compounds of the formula (I) are particularly suitable for modifying the dielectric anisotropy (Δε) even when added in small amounts.

The invention thus relates to compounds of the formula (I) and to the use of these compounds as components of liquid-crystalline mixtures and liquid-crystal mixtures comprising compounds of the formula (I).

The compounds of the formula (I) can be employed in various liquid-crystal mixtures. In the case of nematic mixtures, they are particularly suitable for "active matrix displays" (AM-LCDs) (see, for example, C. Prince, Seminar Lecture Notes, Volume I, p. M-3/3-M-22, SID International Symposium 1997, B. B: Bahadur, Liquid Crystal Applications and Uses, Vol. 1, p. 410, World Scientific Publishing, 1990, E. Lüder, Recent Progress of AMLCD's, Proceedings of the 15$^{th}$ International Display Research Conference, 1995, p. 9–12) and "in-plane switching displays" (IPS-LCDs), and in the case of smectic liquid-crystal mixtures, they are suitable for smectic (ferroelectric or antiferroelectric) displays.

Further components of liquid-crystal mixtures which comprise compounds of the formula (I) according to the invention are preferably selected from the known compounds having smectic and/or nematic and/or cholesteric phases. Mixture components which are suitable in this sense are mentioned, in particular, in WO 00/36054, DE-A-19 531 165 and EP-A-0 893 424, which are expressly incorporated herein by way of reference.

The invention therefore also relates to liquid-crystal mixtures which comprise at least one compound of the formula (I), preferably in an amount of from 1 to 40% by weight, based on the liquid-crystal mixture. The mixtures preferably comprise at least 3 further components. In addition, the invention also relates to electrooptical display elements (displays) which contain the mixtures according to the invention.

Preference is given to displays which contain nematic or smectic (ferroelectric or antiferroelectric) mixtures according to the invention in combination with active matrix elements.

The display elements (displays) according to the invention are usually constructed in such a way that a liquid-crystal layer is enclosed on both sides by layers which are usually, in this sequence starting from the LC layer, at least one alignment layer, electrodes and a limiting sheet (for example made of glass). In addition, they may contain spacers, adhesive frames, polarizers and, for color displays, thin color-filter layers. Further possible components are antireflection, passivation, compensation and barrier layers as well as electrical non-linear elements, such as thin-film transistors (TFTs) and metal-insulator-metal (MIM) elements. The construction of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

Possible synthesis routes to compounds of the formula (I) are indicated by way of example in the following schemes, with other processes also being feasible and possible.

The following abbreviations are used:
n-BuLi n-butyllithium
DCC dicyclohexylcarbodiimide
DDQ 2,3-dichloro-5,6-dicyano-p-benzoquinone
DEAD diethyl azodicarboxylate (azodicarboxylic acid diethyl ester)
Diglyme diethylene glycol dimethyl ether
DMAP 4-(dimethylamino)pyridine
DME dimethoxyethane
DMF N,N-dimethylformamide
KOtBu potassium tert-butoxide
LICOR organolithium compound+potassium tert-butoxide
LiTMP lithium 2,2,6,6-tetramethylpiperidide
MTBE tert-butyl methyl ether
NMP N-methylpyrrolidone
4-TsOH 4-toluenesulfonic acid Scheme 1

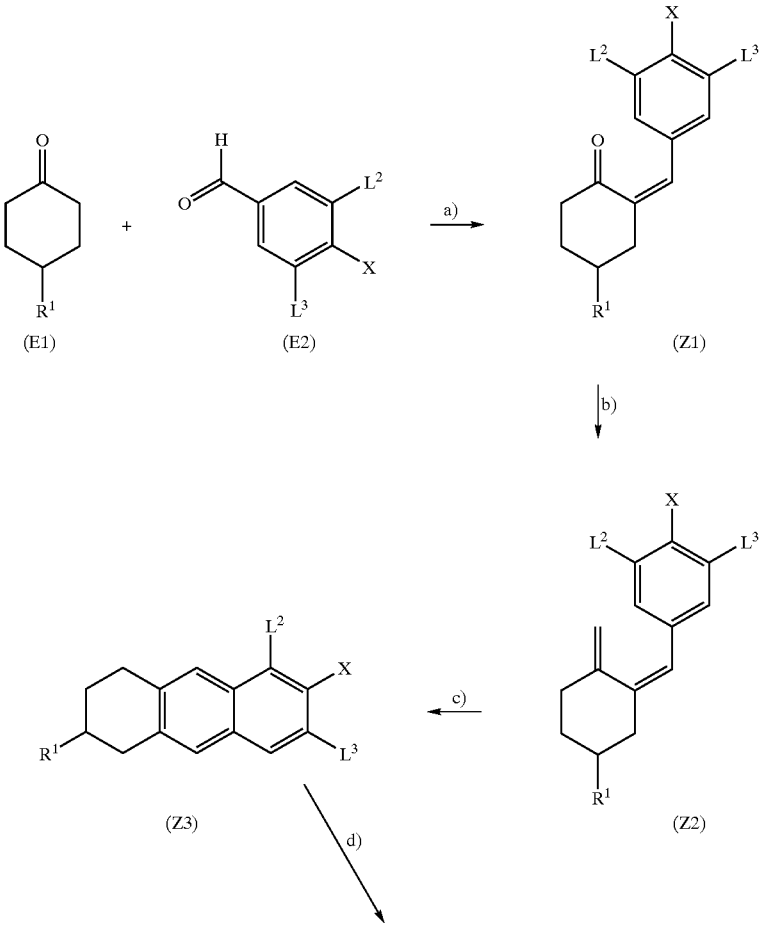

-continued

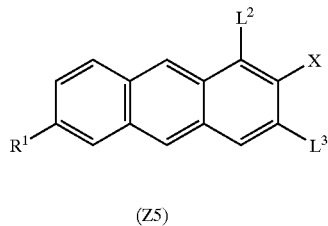

(Z5)

a) analogously to J.Org.Chem. 22, 1161 (1957)
b) 1. [(PPh3)CH3]Br/BuLi 2. (Z1) 3. H2O analogously to J.Org.Chem. 56, 989 (1991)
c) hv, benzene analogously to J.Org.Chem. 56, 989 (1991)
d) DDQ analogously to J.Chem.Soc. 1954, 3569

The starting materials (E1) required for the synthesis of (I) are known from the literature and are for the most part commercially available:
4-methylcyclohexanone [589-92-4]; 4-ethylcyclohexanone [5441-51-0];
4-propylcyclohexanone [40649-36-3]; 4-butylcyclohexanone [61203-82-5];
4-pentylcyclohexanone [61203-83-6]; 4-hexylcyclohexanone [5441-57-6];
4-heptylcyclohexanone [16618-75-0]; 4-(4-methylcyclohexyl)cyclohexanone [151772-66-6]; 4-(4-ethylcyclohexyl)cyclohexanone [150763-46-5];
4-(4-propylcyclohexyl)cyclohexanone [82832-73-3];
4-(4-butylcyclohexyl)cyclohexanone [92413-47-3];
4-(4-pentylcyclohexyl)cyclohexanone [87625-10-3];
4-(4-hydroxyphenyl)cyclohexanone [105640-07-1]
Cyclohexanes containing specific radicals, for example cyclopropyl or dimethylsilyl, can be obtained starting from cyclohexane-1,4-dione monoethylene ketal [4746-97-8].

The following starting materials (E2) are known from the literature and some are commercially available:
X=H, $L^1=L^3=F$ 3,5-difluorobenzaldehyde [32085-88-4]
X=F, $L^1=L^3=F$ 3,4,5-trifluorobenzaldehyde [132123-54-7]
X=OCH$_3$, $L^1=L^3=F$ 3,5-difluoro-4-methoxybenzaldehyde [654-11-5]
X=NCS, $L^1=L^3=F$ 3,5-difluoro-4-isothiocyanatobenzaldehyde [243651-31-2]
X=Br, $L^1=L^3=F$ 4-bromo-3,5-difluorobenzaldehyde [135564-22-6]
X=Cl, $L^1=L^3=F$ 4-chloro-3,5-difluorobenzaldehyde can be prepared analogously to the bromine compound in accordance with Liq. Crystals 23, 575(1997).
X=CF$_3$, $L^1=L^3=F$ can be prepared from 3,5-difluoro-4-trifluoromethylbenzoic acid [261945-09-9], which is known from the literature, by a Rosenmund reduction analogously to J. Am. Chem. Soc. 108, 2608(1986).
X=OCHF$_2$, $L^1=L^3=F$ can be prepared from 3,5-difluoro-4-difluoromethoxybenzoic acid [176508-82-0], which is known from the literature, by a Rosenmund reduction analogously to J. Am. Chem. Soc. 108, 2608(1986).
X=H, $L^3=L^4=F$ 2,3-difluorobenzaldehyde [2646-91-5]
X=F, $L^3=L^4=F$ 2,3,4-trifluorobenzaldehyde [161793-17-5]
After steps a), b) and c) have been carried out, the compounds (Ia) corresponding to (Z3) with X=F, (Ib) corresponding to (Z3) with X=OCF$_3$ and (Id) corresponding to (Z3) with X=Cl are obtained directly.

Scheme 2

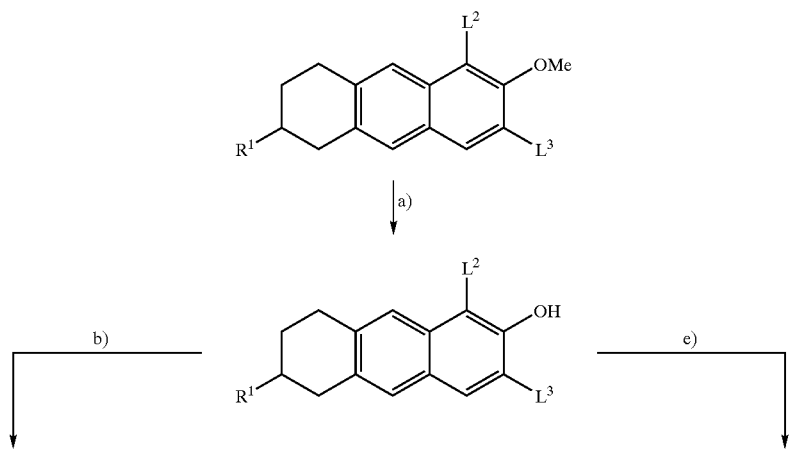

-continued

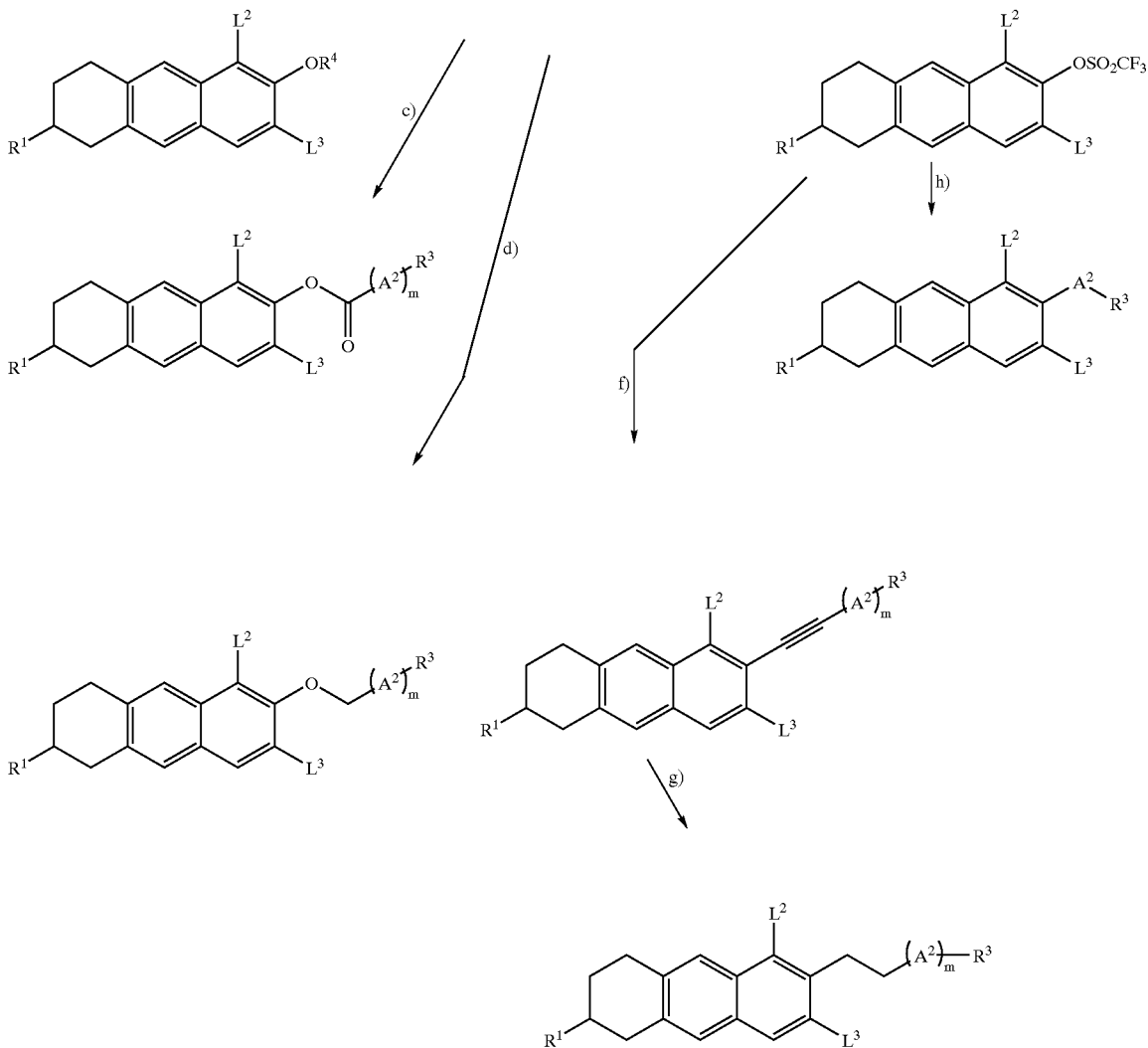

a) HBr/CH$_3$COOH
b) R$^4$Br/K$_2$CO$_3$/MEK
c) R$^3$—(A$^2$)$_m$—COOH/DCC/DMAP/CH$_2$Cl$_2$
d) R$^3$—(A$^2$)$_m$—CH$_2$OH/DEAD/PPh$_3$/THF
e) (F$_3$CSO$_2$)$_2$O/pyridine
f) R$^3$—(A$^2$)$_m$—C≡CH/Pd(PPh$_3$)$_2$Cl$_2$/CuI/NEt$_3$
g) H$_2$/Pd—C/THF
h) R$^3$—A$^2$—B(OH)$_2$/Pd(PPh$_3$)$_4$/Na$_2$CO$_3$/toluene/EtOH/H$_2$O (Ic) corresponding to (Z4) with X=CN can be obtained analogously from (Z3) with X=Br by reaction with CuCN/NMP analogously to WO 91/05780.

(Ie) and (If) can be obtained from (Z3) with X=Br (or X=OCH$_3$, as shown in Scheme 2) by Suzuki reaction with 3,4,5-trifluorophenylboronic acid {in the case of (Ie)} or 3,5-difluoro-4-trifluoromethoxyphenylboronic acid {in the case of (If)}.

(Ig) can be obtained in accordance with Scheme 1 by reacting a compound (Z3) with L$^2$=F and L$^3$=H with an electrophilic fluorinating agent, for example F-TEDA-BF$_4$ analogously to Taylor et al., Tetrahedron 55, 12431 (1999).

Further compounds of the formula (I) can be prepared by functionalization of corresponding intermediates (Z3); shown by way of example in Scheme 2 for the case (Z3)=OCH$_3$, shown by way of example in Scheme 3 for the case (Z3)=H or (Z3)=Br, if (E2) is 4-bromo-3,5-difluorobenzaldehyde.

Scheme 3
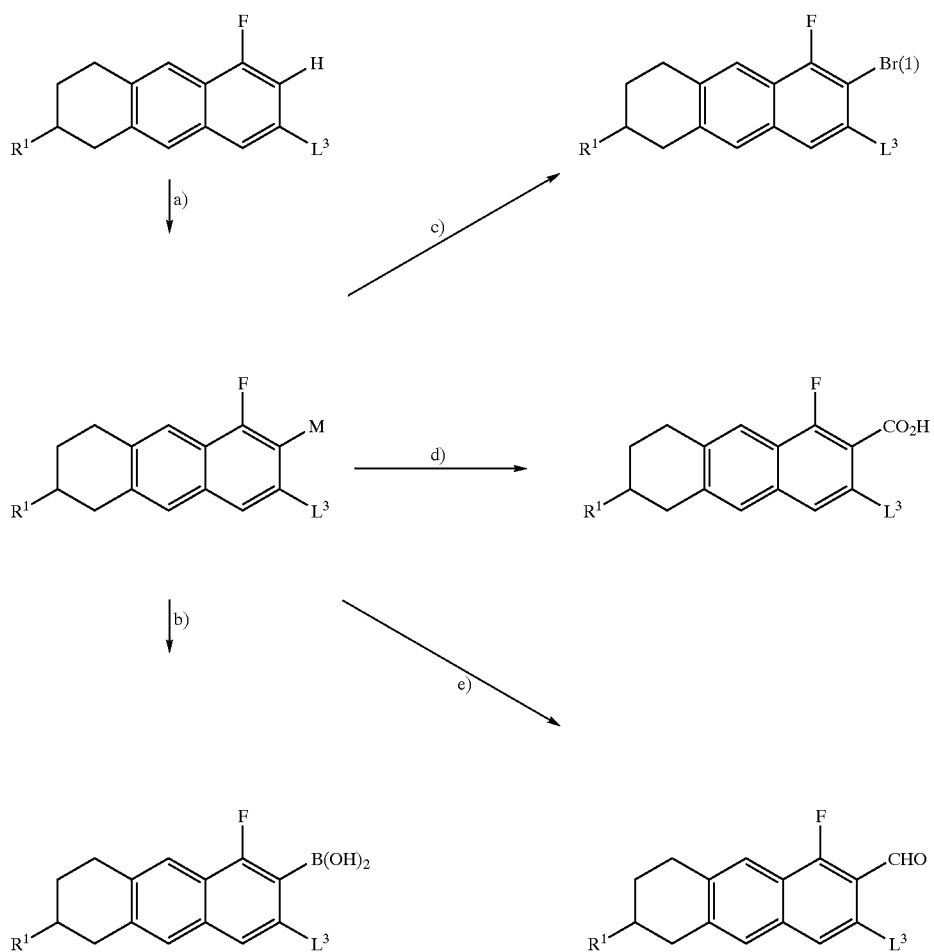
M = Li, K  a) n-BuLi/THF/hexane or n-BuLi/KOtBu/THF/hexane or sec-BuLi/THF/cyclohexane or LiTMP/THF/hexane  b) 1. B(OMe)$_3$ 2. H$_3$O$^+$
c) Br$_2$ (or I$_2$)  d) 1. CO$_2$ 2. H$_3$O$^+$  e) 1. DMF 2. H$_3$O$^+$
Scheme 4
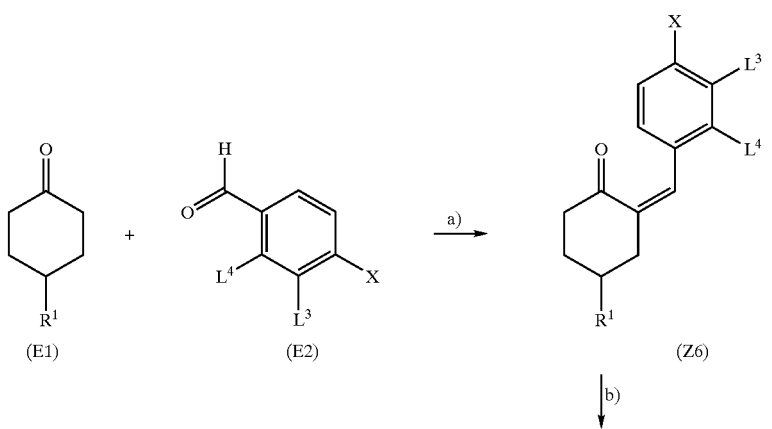

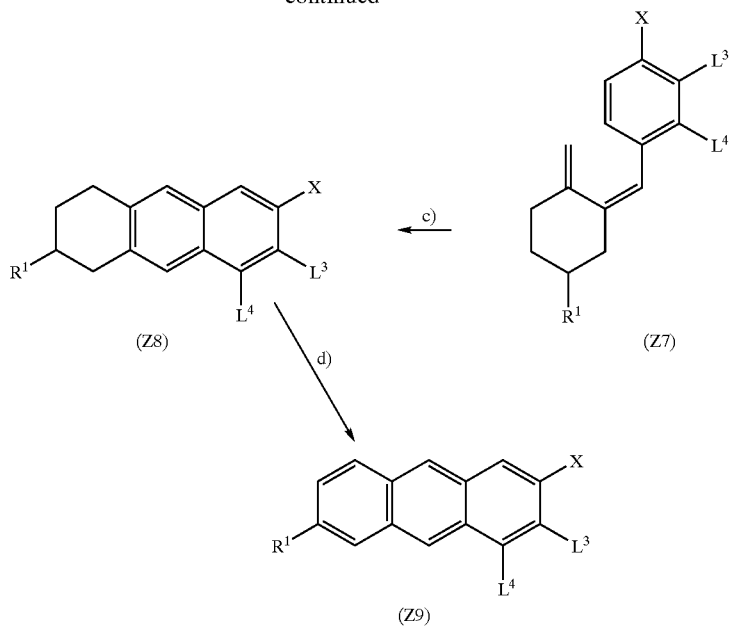

(Z8)          (Z7)

(Z9)

a) analogously to J.Org.Chem. 22, 1161 (1957)
b) 1. [(PPh₃)CH₃]Br/BuLi 2. (Z6) 3. H₂O analogously to J.Org.Chem. 56, 989 (1991)
c) hν, benzene analogously to J.Org.Chem. 56, 989 (1991)
d) DDQ analogously to J.Chem.Soc. 1954, 3569

The further conversion of the functional derivatives of the compounds (I) in the respective schemes into the end compounds—for example by esterification of the carboxylic acid, by Suzuki reaction of the boronic acid, by Wittig reactions of the aldehyde or acetalization (to dioxanes) of the aldehyde—are carried out by methods which are familiar to the person skilled in the art.

The preparation of the benzoic acids, cyclohexanecarboxylic acids and phenylacetylenes, phenylboronic acids, bromobenzenes and 2-alkylpropane-1,3-diols which are needed for the syntheses in accordance with Schemes 1, 2 and 3 and are, for example, alkyl-, alkenyl- or alkoxy-substituted and are optionally additionally fluorinated, and their reactions are known to the person skilled in the art and are described, for example, in WO 96/00710, WO 96/30344, Liq. Cryst. 1995, 18, 1, Mol. Cryst. Liq. Cryst. 1991, 204, 43, Liq. Cryst. 1997, 23, 389, Synthesis 1996, 589, WO 92/11241, EP-A 0665825 and J. Mater. Chem. 1999, 9, 1669. Correspondingly substituted benzyl alcohols and (hydroxymethyl)cyclohexanes $R^3$-$A^2$-$CH_2OH$ can be obtained, for example, from the corresponding benzoic acids or cyclohexane-carboxylic acids $R^3$-$A^2$-COOH by reduction with lithium aluminum hydride (general working procedure: Organikum [Synthetic Organic Chemistry], VEB Deutscher Verlag der Wissenschaften, 15th Edn., Berlin, 1984, Chapter 7.3.4). Bromination thereof using phosphorus tribromide (analogously to J. Org. Chem. 1984, 49, 2534-2540) gives the benzyl bromides or (bromomethyl)cyclohexanes $R^3$-$A^2$-$CH_2$Br. Subsequent reaction with triphenylphosphine in xylene gives the triphenylphosphonium bromides $R^3$-$A^2$-$CH_2$—P($Ph_3$)Br. Correspondingly substituted benzaldehydes and cyclohexanecarboxaldehydes $R^3$-$A^2$-CHO are obtainable, for example, by reduction of the respective carboxylic acid ester $R^3$-$A^2$-COOR (Bull. Korean. Chem. Soc. 1999, 20, 1373) or oxidation of the abovementioned benzyl alcohols and (hydroxymethyl)cyclohexanes $R^3$-$A^2$-$CH_2OH$ (Tetrahedron Lett. 1968, 30, 3363).

The synthesis of specific radicals is carried out, for example, in accordance with DE-A-19 528 085, DE-A-19 532 292 and DE-A-19 654 487. Compounds of the formula (I) according to the invention with a 1-cyclohexene-1,4-diyl or 2-fluoro-1-cyclohexene-1,4-diyl or 4-fluoro-3-cyclohexen-1-yl unit are prepared as described in Liq. Cryst. 1997, 23, 69, DE-A-4 427 266, DE-A-19 607 996, DE-A-19 528 665 and EP-A-0 736 513. Regarding the synthesis of further specific radicals $R^1$ and $R^2$, reference is additionally made, for example, to EP-A-0 355 008 (for compounds with silicon-containing side chains), U.S. Pat. No. 4,798,680 (for optically active compounds with a 2-fluoroalkoxy unit), EP-A-0 552 658 (for compounds with cyclohexylpropionic acid esters) and EP-A-0 318 423 (for compounds with cyclopropyl groups in the side chain).

The invention is explained in greater detail by the following examples.

EXAMPLE 1

2-Propyl-5,6,7-trifluoro-1,2,3,4-tetrahydroanthracene [(Ia) with $R^4$=propyl]

A mixture of 5 mmol of methyltriphenylphosphonium bromide and 5 mmol of butyllithium in 25 ml of tetrahydrofuran which has been reacted to completion at 0° C. was treated over the course of 10 minutes with a solution of 4.5 mmol of 4-propyl-2-(3,4,5-trifluorobenzylidene) cyclohexanone [prepared from 4-propyl-cyclohexanone and 3,4,5-trifluorobenzaldehyde analogously to Walton, J. Org. Chem. 22, 1161 (1957)] in 5 ml of tetrahydrofuran. After 4 hours at room temperature, 50 ml of water were added, the mixture was extracted twice with 25 ml of tert-butyl methyl ether each time, the extract was washed with water and evaporated in a rotary evaporator, and the residue was chromatographed over silica gel with heptane. The resultant crude product [(Z2) from Scheme 1 with $R^1$=propyl, $L^2$=$L^3$=F, X=F] was dissolved in 1 l of benzene and irradiated with a 450 W UV lamp with cooling in a circulation apparatus. After 8 hours, the reaction solution was evaporated in a rotary evaporator, and the residue was chromatographed over silica gel with heptane/ethyl acetate 9:1. Recrystallization from acetonitrile gave colorless crystals.

The following were obtained analogously:
2-methyl-5,6,7-trifluoro-1,2,3,4-tetrahydroanthracene
2-ethyl-5,6,7-trifluoro-1,2,3,4-tetrahydroanthracene
2-butyl-5,6,7-trifluoro-1,2,3,4-tetrahydroanthracene
2-pentyl-5,6,7-trifluoro-1,2,3,4-tetrahydroanthracene
2-(4-ethylcyclohexyl)-5,6,7-trifluoro-1,2,3,4-tetrahydroanthracene
5,7-difluoro-2-methyl-6-trifluoromethoxy-1,2,3,4-tetrahydroanthracene
5,7-difluoro-2-ethyl-6-trifluoromethoxy-1,2,3,4-tetrahydroanthracene
5,7-difluoro-2-propyl-6-trifluoromethoxy-1,2,3,4-tetrahydroanthracene
5,7-difluoro-2-butyl-6-trifluoromethoxy-1,2,3,4-tetrahydroanthracene
5,7-difluoro-2-pentyl-6-trifluoromethoxy-1,2,3,4-tetrahydroanthracene 5,7-Difluoro-2-propyl-1,2,3,4-tetrahydroanthracene is obtained analogously to Example 1 (high-viscosity oil; $^1$H-NMR (300 MHz, $CDCl_3$/TMS): δ=0.94 (t, 3 H), 1.1–2.1 (m, 7 H), 2.55 (dd, 1 H), 3.00 (m, 3 H), 6.84 (dd, 1 H), 7.12 (d, 1 H), 7.45 (s, 1 H), 7.72 (s, 1 H)—$^{19}$F-NMR (282.4 MHz, $^1$H broad-band decoupled, $CDCl_3$/$CFCl_3$): δ=–114.84 (d, $^4J_{FF}$=7 Hz), –120.24 (d, $^4J_{FF}$=7 Hz).

4-Bromo-5,7-difluoro-2-propyl-1,2,3,4-tetrahydroanthracene can be obtained analogously.

The following can be prepared therefrom:
6-cyano-5,7-difluoro-2-propyl-1,2,3,4-tetrahydroanthracene
5,7-difluoro-2-propyl-6-(3,4,5-trifluorophenyl)-1,2,3,4-tetrahydroanthracene The following can be obtained by a homologous procedure:
6-cyano-2-methyl-5,7-difluoro-1,2,3,4-tetrahydroanthracene
6-cyano-5,7-difluoro-2-ethyl-1,2,3,4-tetrahydroanthracene
2-butyl-6-cyano-5,7-difluoro-1,2,3,4-tetrahydroanthracene
6-cyano-5,7-difluoro-2-pentyl-1,2,3,4-tetrahydroanthracene
2-methyl-5,7-difluoro-6-(3,4,5-trifluorophenyl)-1,2,3,4-tetrahydroanthracene
2-ethyl-5,7-difluoro-6-(3,4,5-trifluorophenyl)-1,2,3,4-tetrahydroanthracene
2-butyl-5,7-difluoro-6-(3,4,5-trifluorophenyl)-1,2,3,4-tetrahydroanthracene
2-pentyl-5,7-difluoro-6-(3,4,5-trifluorophenyl)-1,2,3,4-tetrahydroanthracene
5,7-difluoro-6-(3,5-difluoro-4-trifluoromethoxyphenyl)-2-methyl-1,2,3,4-tetrahydroanthracene
5,7-difluoro-6-(3,5-difluoro-4-trifluoromethoxyphenyl)-2-ethyl-1,2,3,4-tetrahydroanthracene
5,7-difluoro-6-(3,5-difluoro-4-trifluoromethoxyphenyl)-2-propyl-1,2,3,4-tetrahydroanthracene
2-butyl-5,7-difluoro-6-(3,5-difluoro-4-trifluoromethoxyphenyl)-1,2,3,4-tetrahydroanthracene
5,7-difluoro-6-(3,5-difluoro-4-trifluoromethoxyphenyl)-2-pentyl-1,2,3,4-tetrahydroanthracene

EXAMPLE 2

2-Propyl-5,6,7-trifluoroanthracene [(Ih) with $R^6$=propyl]

A solution of 2 mmol of the compound from Example 1 is refluxed with the equimolar amount of 2,3-dichloro-5,6-dicyano-p-benzoquinone in toluene until the reaction is complete. After conventional work-up, the product is chromatographed over silica gel in toluene, the product-containing fractions are combined and evaporated in a rotary evaporator, and the residue is recrystallized from acetonitrile.

The following are obtained analogously:
2-methyl-5,6,7-trifluoroanthracene
2-ethyl-5,6,7-trifluoroanthracene
2-butyl-5,6,7-trifluoroanthracene
2-pentyl-5,6,7-trifluoroanthracene and analogous 6-alkyl-1,2,3-trifluoroanthracenes

EXAMPLE 3

A nematic test mixture MLC-9000-100 (manufacturer: Merck KGaA, Darmstadt) is mixed with 5% of the compound from Example 1; the following improvements are obtained compared with the comparative values for the mixture MLC-9000-100 given in brackets: optical anisotropy Δn=0.120 (0.1137); rotational viscosity γ=191 mPas (201 mPas)

EXAMPLE 4

A chiral smectic C mixture consisting of

| | |
|---|---|
| 2-(4-heptyloxyphenyl)-5-nonylpyrimidine | 19.6% |
| 5-nonyl-2-(4-octyloxyphenyl)pyrimidine | 19.6% |
| 5-nonyl-2-(4-nonyloxyphenyl)pyrimidine | 19.6% |
| 2-(2,3-difluoro-4-heptyloxyphenyl)-5-nonylpyrimidine | 6.5% |
| 2-(2,3-difluoro-4-octyloxyphenyl)-5-nonylpyrimidine | 6.5% |
| 2-(2,3-difluoro-4-nonyloxyphenyl)-5-nonylpyrimidine | 6.5% |
| 5-hexyloxy-2-(4-hexyloxyphenyl)pyrimidine | 19.6% |
| (S)-4-[4'-(2-fluoroctyloxy)biphenyl-4-yl]-1-heptylcyclohexanecarbonitrile | 2.0% | is mixed with 5% of the compound from Example 1; the resultant mixture exhibits a 9% improvement in response time.

EXAMPLE 5

2-Ethyl-7,8-difluoro-6-propyl-1,2,3,4-tetrahydroanthracene [(Im) with $R^7$=ethyl, $R^8$=propyl]

A mixture of 5 mmol of methyltriphenylphosphonium bromide and 5 mmol of butyllithium in 25 ml of tetrahydrofuran which has been reacted to completion at 0° C. was treated over the course of 10 minutes with a solution of 4.5 mmol of 4-ethyl-2-(2,3-difluorobenzylidene)cyclohexanone [prepared from 4-ethylcyclohexanone and 2,3-difluorobenzaldehyde analogously to Walton, J. Org. Chem. 22, 1161 (1957)] in 5 ml of tetrahydrofuran. After 4 hours at room temperature, the mixture was introduced into 50 ml of water, the mixture was extracted twice with 25 ml of tert-butyl methyl ether each time, the extract was washed with water and evaporated in a rotary evaporator, and the residue was chromatographed over silica gel with heptane. The resultant crude product [(Z6) from Scheme 5 with $R^1$=ethyl, $L^3$=$L^4$=F, X=H) was dissolved in 1 l of benzene and irradiated with a 450 W UV lamp with cooling in a circulation apparatus. After 8 hours, the reaction solution was evaporated in a rotary evaporator, the residue was chromatographed over silica gel with heptane/dichloromethane 9:1. The resultant 2-ethyl-7,7-difluoro-1,2,3,4-tetrahydroanthracene was reacted with 1.1 equivalents of sec-butyllithium in tetrahydrofuran at –75° C. and subsequently with 1.2 equivalents of 1-bromopropane. After conventional work-up, the product was purified by chromatography (silica gel, heptane/dichloromethane 9:1), and the crude product was recrystallized from acetonitrile.

The following are obtained analogously:
2-methyl-7,8-difluoro-6-propyl-1,2,3,4-tetrahydroanthracene
2-ethyl-7,8-difluoro-6-propyl-1,2,3,4-tetrahydroanthracene
2-butyl-7,8-difluoro-6-propyl-1,2,3,4-tetrahydroanthracene
2-pentyl-7,8-difluoro-6-propyl-1,2,3,4-tetrahydroanthracene
2-methyl-7,8-difluoro-6-methyl-1,2,3,4-tetrahydroanthracene
2-ethyl-7,8-difluoro-6-methyl-1,2,3,4-tetrahydroanthracene
2-propyl-7,8-difluoro-6-methyl-1,2,3,4-tetrahydroanthracene
2-butyl-7,8-difluoro-6-methyl-1,2,3,4-tetrahydroanthracene
2-pentyl-7,8-difluoro-6-methyl-1,2,3,4-tetrahydroanthracene
2-methyl-7,8-difluoro-6-ethyl-1,2,3,4-tetrahydroanthracene
2-ethyl-7,8-difluoro-6-ethyl-1,2,3,4-tetrahydroanthracene
2-propyl-7,8-difluoro-6-ethyl-1,2,3,4-tetrahydroanthracene
2-butyl-7,8-difluoro-6-ethyl-1,2,3,4-tetrahydroanthracene
2-pentyl-7,8-difluoro-6-ethyl-1,2,3,4-tetrahydroanthracene
2-methyl-7,8-difluoro-6-butyl-1,2,3,4-tetrahydroanthracene
2-ethyl-7,8-difluoro-6-butyl-1,2,3,4-tetrahydroanthracene
2-propyl-7,8-difluoro-6-butyl-1,2,3,4-tetrahydroanthracene
2-butyl-7,8-difluoro-6-butyl-1,2,3,4-tetrahydroanthracene
2-pentyl-7,8-difluoro-6-butyl-1,2,3,4-tetrahydroanthracene
2-methyl-7,8-difluoro-6-pentyl-1,2,3,4-tetrahydroanthracene
2-ethyl-7,8-difluoro-6-pentyl-1,2,3,4-tetrahydroanthracene
2-propyl-7,8-difluoro-6-pentyl-1,2,3,4-tetrahydroanthracene
2-butyl-7,8-difluoro-6-pentyl-1,2,3,4-tetrahydroanthracene
2-pentyl-7,8-difluoro-6-pentyl-1,2,3,4-tetrahydroanthracene.

The following are obtained analogously starting from 2,3,4-trifluorobenzaldehyde:
2-methyl-6,7,8-trifluoro-1,2,3,4-tetrahydroanthracene
2-ethyl-6,7,8-trifluoro-1,2,3,4-tetrahydroanthracene
2-propyl-6,7,8-trifluoro-1,2,3,4-tetrahydroanthracene
2-butyl-6,7,8-trifluoro-1,2,3,4-tetrahydroanthracene
2-pentyl-6,7,8-difluoro-1,2,3,4-tetrahydroanthracene.

EXAMPLE 6

2-Ethyl-7,8-difluoro-6-propylanthracene [(Iq) with $R^8$=propyl, $R^9$=ethyl]

A solution of 2 mmol of the compound from Example 5 is refluxed with the equimolar amount of 2,3-dichloro-5,6-dicyano-p-benzoquinone in toluene until the reaction is complete. After conventional work-up, the product is chromatographed over silica gel in toluene, the product-containing fractions are combined and evaporated in a rotary evaporator, and the residue is recrystallized from acetonitrile.

The following are obtained analogously:
2-methyl-7,8-difluoro-6-propylanthracene
2-ethyl-7,8-difluoro-6-propylanthracene
2-butyl-7,8-difluoro-6-propylanthracene
2-pentyl-7,8-difluoro-6-propylanthracene
2-methyl-7,8-difluoro-6-methylanthracene
2-ethyl-7,8-difluoro-6-methylanthracene
2-propyl-7,8-difluoro-6-methylanthracene
2-butyl-7,8-difluoro-6-methylanthracene
2-pentyl-7,8-difluoro-6-methylanthracene
2-methyl-7,8-difluoro-6-ethylanthracene
2-ethyl-7,8-difluoro-6-ethylanthracene
2-propyl-7,8-difluoro-6-ethylanthracene
2-butyl-7,8-difluoro-6-ethylanthracene
2-pentyl-7,8-difluoro-6-ethylanthracene
2-methyl-7,8-difluoro-6-butylanthracene
2-ethyl-7,8-difluoro-6-butylanthracene
2-propyl-7,8-difluoro-6-butylanthracene
2-butyl-7,8-difluoro-6-butylanthracene
2-pentyl-7,8-difluoro-6-butylanthracene
2-methyl-7,8-difluoro-6-pentylanthracene
2-ethyl-7,8-difluoro-6-pentylanthracene
2-propyl-7,8-difluoro-6-pentylanthracene
2-butyl-7,8-difluoro-6-pentylanthracene
2-pentyl-7,8-difluoro-6-pentylanthracene
2-methyl-6,7,8-trifluoroanthracene
2-ethyl-6,7,8-trifluoroanthracene
2-propyl-6,7,8-trifluoroanthracene
2-butyl-6,7,8-trifluoroanthracene
2-pentyl-6,7,8-difluoroanthracene.

EXAMPLE 7

A nematic test mixture MLC-9000-100 (manufacturer: Merck KGaA, Darmstadt) is mixed with 5% of the compound from Example 5; the following improvements are obtained compared with the comparative values for the mixture MLC-9000-100 given in brackets: optical anisotropy Δn=0.121 (0.1137).

EXAMPLE 8

A chiral smectic C mixture consisting of

| | |
|---|---|
| 2-(4-heptyloxyphenyl)-5-nonylpyrimidine | 19.6% |
| 5-nonyl-2-(4-octyloxyphenyl)pyrimidine | 19.6% |
| 5-nonyl-2-(4-nonyloxyphenyl)pyrimidine | 19.6% |
| 2-(2,3-difluoro-4-heptyloxyphenyl)-5-nonylpyrimidine | 6.5% |
| 2-(2,3-difluoro-4-octyloxyphenyl)-5-nonylpyrimidine | 6.5% |
| 2-(2,3-difluoro-4-nonyloxyphenyl)-5-nonylpyrimidine | 6.5% |
| 5-hexyloxy-2-(4-hexyloxyphenyl)pyrimidine | 19.6% |
| (S)-4-[4'-(2-fluorooctyloxy)biphenyl-4-yl]-1-heptylcyclohexanecarbonitrile | 2.0% | is mixed with 5% of the compound from Example 5; the resultant mixture exhibits a 7% improvement in response time.

What is claimed is:
1. A compound of the formula (I)

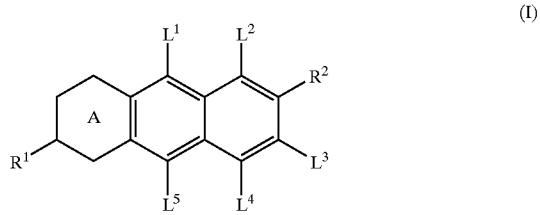

in which:
$L^1$, $L^2$, $L^3$, $L^4$ and $L^5$ are identical or different and are H or F, with the provisos that
a) at least one of $L^1$, $L^2$, $L^3$ $L^4$ and $L^5$ must be F
b) if $L^1$ is F, $L^3$, $L^4$ and $L^5$ must be H
c) if $L^4$ or $L^5$ is F, $L^1$ and $L^2$ must be H,
$R^1$ is a straight-chain or branched alkyl radical having from 1 to 16 carbon atoms or a straight-chain or branched alkenyl radical having from 2 to 16 carbon atoms, in which
a) one or more non-adjacent and non-terminal $CH_2$ groups may be replaced by —O—, —C(=O)O—, —O—C(=O)—, —O—C(=O)—O—, —C(=O)— or —Si(CH$_3$)$_2$—, and/or b) one CH$_2$ group may be replaced by —C≡C—, cyclopropane-1,2-diyl, cyclobutane-1,3-diyl, cyclohexan-1,4-diyl or phenylene-1,4-diyl, and/or c) one or more H atoms may be replaced by F and/or Cl, R$^2$ is hydrogen, F, Cl, CN, —NCS, CF$_3$, CHF$_2$, CH$_2$F, OCF$_3$, OCHF$_2$, OCH$_2$F, OCH$_2$CF$_3$, OCH=CF$_2$ or a straight-chain or branched alkyl radical having from 1 to 12 carbon atoms or a straight-chain or branched alkenyl radical having from 2 to 12 carbon atoms, in which a) one or more non-adjacent and non-terminal CH$_2$ groups may be replaced by —O—, —C(=O)O—, —O—C(=O)—, —O—C(=O)—O—, —C(=O)— or —Si(CH$_3$)$_2$—, and/or b) one CH$_2$ group may be replaced by —C≡C—, cyclopropane-1,2-diyl or cyclobutane-1,3-diyl, and/or c) one or more H atoms may be replaced by F and/or Cl and/or the -M$^2$-A$^2$-R$^3$ group, in which M$^2$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond, A$^2$ is 1,4-phenylene, in which one or two H atoms may be replaced by F, Cl, CN and/or OCF$_3$ or up to three H atoms may be replaced by F, 1,4-cyclohexylene, in which one or two H atoms may be replaced by CH$_3$ and/or F, 1-cyclohexene-1,4-diyl, in which one H atom may be replaced by CH$_3$ or F, or 1,3-dioxane-2,5-diyl, R$^3$ has the same possible meanings as R$^2$, with the exception of -M$^2$-A$^2$-R$^3$,

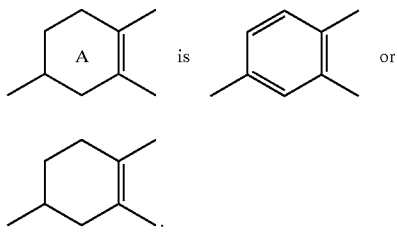

is

2. A compound as claimed in claim 1 conforming to the formulae (Ia) to (It)

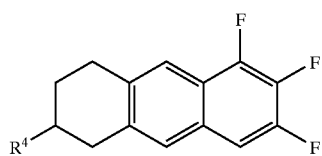 (Ia)

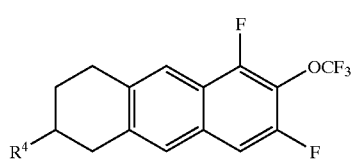 (Ib)

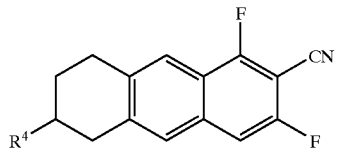 (Ic)

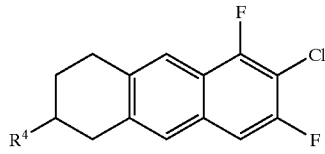 (Id)

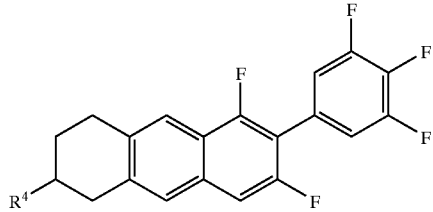 (Ie)

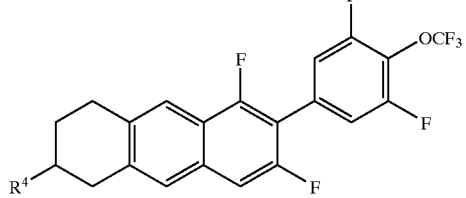 (If)

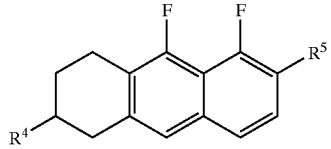 (Ig)

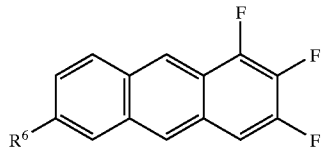 (Ih)

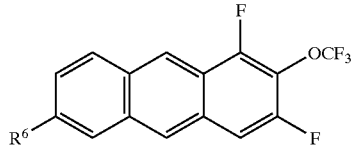 (Ii)

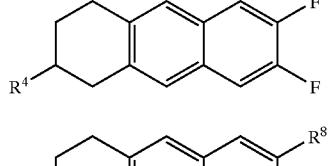 (Ik)

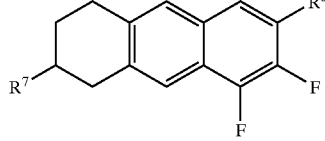 (Im)

-continued

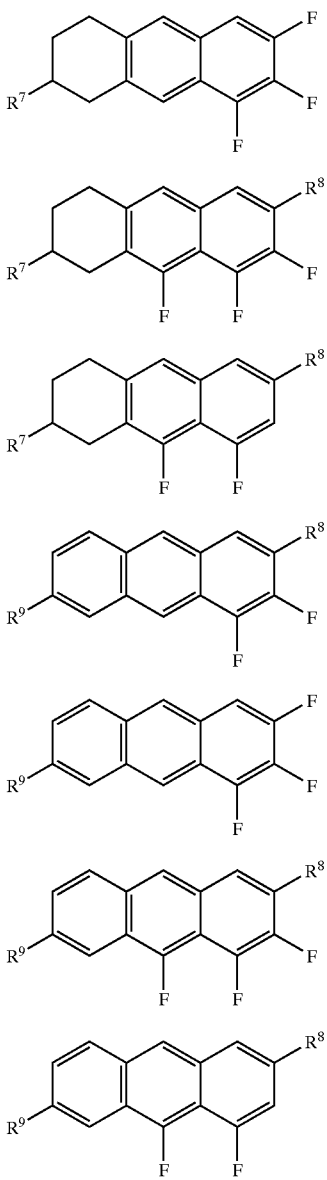

in which:
R⁴ is a straight-chain or branched alkyl radical having from 1 to 16 carbon atoms or a straight-chain or branched alkenyl radical having from 2 to 16 carbon atoms, in which one non-terminal CH₂ group may be replaced by —O— and/or one CH₂ group may be replaced by cyclohexane-1,4-diyl or phenylene-1,4-diyl, R⁵ is hydrogen, a straight-chain or branched alkyl radical having from 1 to 12 carbon atoms or a straight-chain or branched alkenyl radical having from 2 to 12 carbon atoms, in which
  a) one or more non-adjacent and non-terminal CH₂ groups may be replaced by —O—, —C(=O)O—, —O—C(=O)— or —Si(CH₃)₂—, and/or
  b) one CH₂ group may be replaced by —C≡C—, cyclopropane-1,2-diyl or cyclobutane-1,3-diyl, and/or
  c) one or more H atoms may be replaced by F and/or Cl, or the -M²-A²-R³ group, in which M² is —CO—O—, —O—CO—, —CH₂—O—, —O—CH₂—, —CF₂—O—, —O—CF₂—, —CH₂—CH₂—CO—O—, —O—CO—CH₂—CH₂—, —CH₂—CH₂—, —CF₂—CF₂—, —(CH₂)₄—, —OC(=O)CF=CF—, or a single bond, A² is 1,4-cyclohexylene, in which one or two H atoms may be replaced by CH₃ and/or F, 1-cyclohexene-1,4-diyl, in which one H atom may be replaced by CH₃ or F, or 1,3-dioxane-2,5-diyl, R³ is hydrogen, a straight-chain or branched alkyl radical having from 1 to 12 carbon atoms or a straight-chain or branched alkenyl radical having from 2 to 12 carbon atoms, in which
  a) one or more non-adjacent and non-terminal CH₂ groups may be replaced by —O—, —C(=O)O—, —O—C(=O)—, or —Si(CH₃)₂—, and/or
  b) one CH₂ group may be replaced by —C≡C—, cyclopropane-1,2-diyl or cyclobutane-1,3-diyl, and/or
  c) one or more H atoms may be replaced by F and/or Cl, R⁶ is a straight-chain or branched alkyl radical having from 1 to 12 carbon atoms, in which
  a) one or more non-adjacent and non-terminal CH₂ groups may be replaced by —O—, —C(=O)O—, —O—C(=O)—, or —Si(CH₃)₂—, and/or
  b) one CH₂ group which is not adjacent to the ring system may be replaced by —C≡C— or —CH=CH—, and/or
  c) one —CH₂— group may be replaced by cyclopropane-1,2-diyl, cyclobutane-1,3-diyl or cyclohexane-1,4-diyl or 1,3-dioxane-2,5-diyl, and/or
  d) one or more H atoms may be replaced by F and/or Cl, R⁷ is a straight-chain or branched alkyl radical having from 1 to 16 carbon atoms or a straight-chain or branched alkenyl radical having from 2 to 16 carbon atoms, in which one non-terminal CH₂ group may be replaced by —O— and/or one CH₂ group may be replaced by cyclohexane-1,4-diyl or phenylene-1,4-diyl, R⁸ is hydrogen, a straight-chain or branched alkyl radical having from 1 to 12 carbon atoms or a straight-chain or branched alkenyl radical having from 2 to 12 carbon atoms, in which
  a) one or more non-adjacent and non-terminal CH₂ groups may be replaced by —O—, —C(=O)O—, —O—C(=O)— or —Si(CH₃)₂—, and/or
  b) one CH₂ group may be replaced by —C≡C—, cyclopropane-1,2-diyl or cyclobutane-1,3-diyl, and/or
  c) one or more H atoms may be replaced by F and/or Cl, or the -M³-A³-R¹⁰ group, in which
    M³ is —CO—O—, —O—CO—, —CH₂—O—, —O—CH₂—, —CF₂—O—, —O—CF₂—, —CH₂—CH₂—CO—O—, —O—CO—CH₂—CH₂—, —CH₂—CH₂—, —CF₂—CF₂—, —(CH₂)₄—, —OC(=O)CF=CF— or a single bond,
    A³ is 1,4-cyclohexylene, in which one or two H atoms may be replaced by CH₃ and/or F, 1-cyclohexene-1,4-diyl, in which one H atom may be replaced by CH₃ or F, or 1,3-dioxane-2,5-diyl,
    R¹⁰ is hydrogen, a straight-chain or branched alkyl radical having from 1 to 12 carbon atoms or a straight-chain or branched alkenyl radical having from 2 to 12 carbon atoms, in which
  a) one or more non-adjacent and non-terminal $CH_2$ groups may be replaced by —O—, —C(=O)O—, —O—C(=O)—, or —Si($CH_3$)$_2$—, and/or
  b) one $CH_2$ group may be replaced by —C≡C—, cyclopropane-1,2-diyl or cyclobutane-1,3-diyl, and/or
  c) one or more H atoms may be replaced by F and/or Cl, $R^9$ is a straight-chain or branched alkyl radical having from 1 to 12 carbon atoms, in which
  a) one or more non-adjacent and non-terminal $CH_2$ groups may be replaced by —O—, —C(=O)O—, —O—C(=O)—, or —Si($CH_3$)$_2$—, and/or
  b) one $CH_2$ group which is not adjacent to the ring system may be replaced by —C≡C— or —CH=CH—, and/or
  c) one —$CH_2$— group may be replaced by cyclopropane-1,2-diyl, cyclobutane-1,3-diyl or cyclohexane-1,4-diyl or 1,3-dioxane-2,5-diyl, and/or
  d) one or more H atoms may be replaced by F and/or Cl.

3. A liquid-crystal mixture comprising at least one compound of the formula (I) as claimed in claim 1.

4. A liquid-crystal mixture comprising at least one compound of the formula (I) as claimed in claim 2.

5. A liquid-crystal mixture as claimed in claim 3, which comprises one or more compounds of the formula (I) in an amount of from 1 to 40% by weight, based on the liquid-crystal mixture.

6. A liquid-crystal mixture as claimed in claim 3, wherein the mixture comprises at least three further components having smectic and/or nematic and/or cholesteric phases.

7. A liquid-crystal mixture as claimed in claim 3, which is chiral-smectic.

8. A liquid-crystal mixture as claimed in claim 3, which is nematic or cholesteric.

9. A liquid-crystal display containing a liquid-crystal mixture as claimed in claim 3.

10. A liquid-crystal display where the display is operated in ECB, IPS or VA display mode and contains a liquid-crystal mixture as claimed in claim 8.

11. A liquid-crystal mixture as claimed in claim 4, which comprises one or more compounds of the formula (I) in an amount of from 1 to 40% by weight, based on the liquid-crystal mixture.

12. A liquid-crystal mixture as claimed in claim 4 wherein the mixture comprises at least three further components having smectic and/or nematic and/or cholesteric phases.

13. A liquid-crystal mixture as claimed in claim 4, which is chiral-smectic.

14. A liquid-crystal mixture as claimed in claim 4, which is nematic or cholesteric.

15. A liquid-crystal display containing a liquid-crystal mixture as claimed in claim 4.

16. A liquid-crystal display where the display is operated in ECB, IPS or VA display mode and contains a liquid-crystal mixture as claimed in claim 14.

* * * * *